United States Patent [19]
LaVail et al.

[11] Patent Number: 5,667,968
[45] Date of Patent: Sep. 16, 1997

[54] PREVENTION OF RETINAL INJURY AND DEGENERATION BY SPECIFIC FACTORS

[75] Inventors: Matthew M. LaVail; Roy H. Steinberg, both of San Francisco, Calif.; George D. Yancopoulos, Briarcliff Manor, N.Y.

[73] Assignees: Regeneron Pharmaceuticals, Inc., Tarrytown, N.Y.; Regents of the Univ. of California, Oakland, Calif.

[21] Appl. No.: 334,859

[22] Filed: Nov. 4, 1994

Related U.S. Application Data

[63] Continuation of Ser. No. 836,090, Feb. 14, 1992, abandoned, which is a continuation-in-part of Ser. No. 691,612, Apr. 25, 1991, abandoned, which is a continuation-in-part of Ser. No. 570,657, Aug. 20, 1990, Pat. No. 5,229,500, which is a continuation-in-part of Ser. No. 400,591, Aug. 30, 1989, Pat. No. 5,180,820.

[51] Int. Cl.$^6$ .................................................. A61K 38/18
[52] U.S. Cl. .................................................. 514/12; 514/2
[58] Field of Search ........................... 514/2, 12; 530/350, 530/399

[56] References Cited

U.S. PATENT DOCUMENTS

| | | | |
|---|---|---|---|
| 5,011,914 | 4/1991 | Collins et al. | 530/399 |
| 5,169,764 | 12/1992 | Shooter et al. | 435/69.7 |

OTHER PUBLICATIONS

The Merck manual, 14th edition, ©1982, pp. 2000–2005.
Rapp "Handbook of Neurotoxicity" (Chang and Dyer, eds) pp. 963–1003, Marcel Dekker Inc, NY (1995).
Lieberman International Review of Neurobiology 14. (1971) 49–124.
Merck Manual of Diagnosis & Therapy, 16th ed. (1992), Berkow et al, eds. pp. 2383–2386.
Mey et al Brain Res. 602 304–317 (1993).
Manthorpe et al in: Neurotrophic Factors, Loughlin et al, eds. (Academic Press 1993).
The Merck Manual of Diagnosis and Therapy, 15th Edition Robert Berkow, Editor–in–Chief, pp. 2232–2234, 1987.
Marcia Barinaga (1994, May 6). Science vol. 264, pp. 772–774.
BioWorld Today (Jun. 24, 1994) vol. 5, #123, pp. 1–6.
Carmignoto, et al., Effect of NGF on the Survival of Rat Retinal Ganglion Cells Following Optic Nerve Section, J. Neurosci. 9: 1263–1272 (1989).
"Cephalon to Study Retinal Diseases", BioWorld Today, Nov. 10, 1991, p. 3.
Faktorovich, et al., Photoreceptor degeneration in inherited retinal dystrophy delayed by basic fibroblast growth factor, Nature 347: 83–86 (1990).
Faktorovich, et al. Photoreceptor rescue in Retinal Degenerations By Basic Fibroblast Growth Factor, In: Retinal egenerations, R.E. Anderson, J.G. Hollyfield and M.M. LaVail, Eds. CRC Press, Boca Raton, pp. 101–108, 1991.

Faktorovich, et al. Photoreceptor rescue in the RCS rat: Effect of bFGF, aFGF and selected controls, Invest. Ophthal. & Vis. Sci. (Suppl): 595 (1990).
Ferguson, et al. Basic Fibroblast Growth Factor: Receptor–Mediated Internalization, Metabolism, and Anterograde Axonal Transport in Retinal Ganglion Cells, J. Neurosci. 10:2176–2189. (1990).
Johnson, et al., Brain–Derived Neurotrophic Factor Supports the Survival of Cultured Rat Retinal Ganglion Cells, J. Neurosci. 6: 3031–3038 (1986).
LaVail, et al. bFGF protects photoreceptor cells from light damage in the rat, Invest. Ophthal. Vis. Sci. 32 (Suppl):1097 (1991).
McCaffrey, et al., The Survival of Neonatal Rat Retinal Ganglion Cells in vitro is Enhanced in the Presence of Appropriate Parts of the Brain, Exp. Brain Res. 48: 377–386 (1982).
Rodriguez–Tebar, et al., The Survival of Chick Retinal Ganglion Cells in Response to Brain–Derived Neurotrophic Factor Depends on Their Embryonic Age, Dev. Biol. 136: 296–303 (1989).
Schulz, et al., A Retinal Ganglion Cell Neurotrophic Factor Purified from the Superior Colliculus, J. Neurochem. 55: 832–841 (1990).
Silverman, et al., Photoreceptor Transplantation to Dystrophic Retina, In; Retinal Degenerations, (ed. Anderson R.E., LaVail, M.M. and Hollyfield F.G.). CRC Press Inc. Boca Raton, Florida, pp. 321–335 (1991).
Silverman, et al., Transplantation of Photoreceptors to Light Damaged Retina, Inv. Ophthalmology & Visual Science 30: 1684–1690 (1989).
Small, et al. Response of Muller Cells to Growth Factors Alters With Time in Culture, GLIA 4:469–483 (1991).
Steinberg, et al. Basic fibroblast growth factor and photoreceptor regeneration. In: CIBA Symposium on Growth and Development. Ciba Foundation Symposium 160, G.R. Bock and J. Whelan, Eds., John Wiley & Sons, New York pp. 219–232 (1991).
Thanos, et al., Survival and Axonal Elongation of Adult Rat Retinal Ganglion Cells, Eur. J. Neurosci. 1: 19–26 (1989).
Turner, et al., Extract from Brain Stimulates Neurite Outgrowth from Fetal Rat Retinal Explants, Developmental Brain Research, 6 77–83 1983.
"Trial of Growth Factor in Eye Surgery", BioWorld Today 2: 204 p. 3 (1991).

*Primary Examiner*—Stephen G. Walsh
*Assistant Examiner*—Robert C. Hayes
*Attorney, Agent, or Firm*—Gail M. Kempler

[57] ABSTRACT

Photoreceptor injury or cell death (retinal degeneration) is prevented by the introduction into the living mammalian eye of specific, survival-promoting factors. These specific factors prevent damage and degeneration of photoreceptors when introduced into the living eye prior to, during or after exposure to the damaging effects of light and delay photoreceptor damage caused by inherited disease.

8 Claims, 6 Drawing Sheets

PREVENTION OF RETINAL INJURY AND DEGENERATION BY SPECIFIC FACTORS

This is a continuation of application Ser. No. 07/836,090 filed on Feb. 14, 1992, now abandoned, which is a continuation-in-part of application Ser. No. 07/691,612 filed on Apr. 25, 1991, now abandoned, which is a continuation-in-part of application Ser. No. 07/570,657 filed Aug. 20, 1990, now U.S. Pat. No. 5,229,500, which is a continuation-in-part of application Ser. No. 07/400,591 filed on Aug. 30, 1989, U.S. Pat. No. 5,180,820.

The Government has certain rights in this invention pursuant to Grant Nos. EY-01919, EY-06842 and EY-01429 awarded by the National Institute of Health.

INTRODUCTION

The present invention relates to a method of preventing or delaying retinal degeneration caused by exposure to light or other environmental trauma, or by any pathological condition wherein death or injury of retinal neurons or photoreceptors occurs. It is based on the discovery that specific survival promoting factors, when introduced into the living mammalian eye, prevent damage and degeneration of photoreceptors caused by light and on the further discovery that such factors can delay photoreceptor degeneration associated with inherited diseases of the retina.

BACKGROUND OF THE INVENTION

Trophic factors play a major role in neuronal survival and growth during development, in addition to the maintenance of differentiated neurons. Such factors also appear to play a role in the survival and regeneration of injured neurons in the central as well as in the peripheral nervous system.

In mammals, a number of diseases of the retina involve injury or degeneration of retina-associated neurons. Trophic factors capable of rescuing these neurons may provide useful therapies for the treatment of such diseases.

There is some evidence that the neurotrophic factor NGF (nerve growth factor) enables axonal regrowth of retinal ganglion cells in response to optic nerve section. (Carmignoto, et al. J. Neuroscience 9 (1989): 1263-1272). Extracts from pig brain stimulate neurite outgrowth in retinal explants; the outgrowth was shown to be due to a factor other than NGF. (Turner, et al. Dev. Brain Res. 6 (1983) 77-83). BDNF (brain derived neurotrophic factor) purified from brain promotes the survival of retinal ganglion cells in vitro. (Johnson, et al. J. Neuroscience 6 (1986): 3031-3038; Thanos, et al. Eur. J. Neuroscience 1 (1989): 19-26.) Other workers have reported that retinal ganglion cells could be maintained by extracts from the neonatal superior colliculus and that a factor purified from such extracts promotes the survival and growth of retinal ganglion cells in vitro. (Schultz, et al. J. Neurochemistry 55 (1990): 832-303). Moreover, fibroblast growth factors promote the survival of adult rat ganglion cells after application to transected optic nerves (Sievers, et al., Neurosci. Let. 76 (1987): 157-162).

In addition to the survival of retinal ganglion cells, there is some evidence that certain cellular factors may promote the survival and/or regeneration of photoreceptors. Photoreceptors consist of rods and cones which are the photosensitive cells of the retina. The rods contain rhodopsin, the rod photopigment, and the cones contain 3 distinct photopigments, which respond to light and ultimately trigger a neural discharge in the output cells of the retina, the ganglion cells. Ultimately, this signal is registered as a visual stimulus in the visual cortex.

The retinal pigment epithelial (RPE) cells produce, store and transport a variety of factors that are responsible for the normal function and survival of photoreceptors. RPE are multifunctional cells that transport metabolites to the photoreceptors from their blood supply, the chorio capillaris of the eye. The RPE cells also function to recycle vitamin A as it moves between the photoreceptors and the RPE during light and dark adaptation. RPE cells also function as macrophages, phagocytizing the rhythmically-shed tips of the outer segments of rods and cones. Various ions, proteins and water move between the RPE cells and the interphotoreceptor space, and these molecules ultimately effect the metabolism and viability of the photoreceptors.

RCS (Royal College of Surgeons) rats, which have an inherited retinal dystrophy due to mutant gene expression in the RPE, with secondary photoreceptor cell death (Mullen & LaVail, Science 192 (1976): 799-801), provide a useful model system to study the role of trophic factors on the retina. Using such rats, delay of photoreceptor degeneration caused by the inherited defect was obtained by the juxtaposition of normal RPE cells to the photoreceptors before their degeneration both in experimental chimeras (Mullen & LaVail, Science 192 (1976): 799-801) and in transplantation experiments (Li & Turner, Exp. Eye Res. 47: 911-917, 1988). In these experiments, the "rescue" extended beyond the boundaries of the normal RPE cells. These findings suggested the presence of a diffusable factor produced by the RPE cells. It was subsequently determined that subretinal or intravitreal injection of basic fibroblast growth factor (bFGF) resulted in extensive photoreceptor rescue in RCS rats (Faktorovich, et al., Nature 347 (1990): 83-86). Basic FGF was also shown to induce retinal regeneration from the RPE in chick embryos (Park & Hollenberg, Dev. Biol. 134 (1989): 201-205).

Although the results obtained with injection of bFGF were encouraging, therapeutic applications of bFGF could be very limited. Given its mitogenic and angiogenic properties, harmful side effects can be expected. As an example, intravitreal injections of bFGF consistently result in numerous invading macrophages in the inner retina, and occasionally produce a massive proliferative vitreoretinopathy (Faktorovich, et. al, Nature 347 (1990): 83-86). Finally, bFGF is unable to remedy one particular defect seen in RCS rats, which is the inability of the RPE to phagocytosize degenerated neurons.

More limited rescue of photoreceptors in RCS rats has been reported with the injection of phosphate buffered saline (PBS) (Silverman & Hughes, Current Eye Res. 9 (1990): 183-191; Faktorovich, et. al, Nature 347 (1990): 83-86), as well as in surgical controls. Such studies indicated a localized effect caused by the possible release of protective factors from RPE or other cells damaged during injection. In such instances, however, the level of rescue differed quantitatively from that obtained using bFGF, i.e. it was much more restricted to the area of the needle track.

In the albino rat, normal illumination levels of light, if continuous, can cause complete degeneration of photoreceptors. Results obtained using such rats as a model to identify survival enhancing factors appear to correlate well with data obtained using RCS rats. Moreover, different factors can be compared and complications can be assessed more quickly in the light damage model than can be assessed by testing factors in models which are based on the slowly evolving dystrophy of the RCS rat. Furthermore, since the mechanism of cell death in light damage is better defined than that in the RCS rats, the results in the light damage model can be more readily applied to human diseases.

Using albino rats, it has been determined that a number of agents, when administered systemically (intraperitoneally) can be used to ameliorate retinal cell death or injury caused by exposure to light. In general, exposure to light generates oxygen free radicals and lipid peroxidation products. Accordingly, compounds that act as antioxidants or as scavengers of oxygen free radicals reduce photoreceptor degeneration. Agents such as ascorbate (Organisciak et al, Investigative Ophthalmology & Visual Science 26 (1985): 1580–1588), flunarizine (Edward, et al., Laboratory Science 109(1991): 554–562) and dimethylthiourea (Lam, et al., Archives of Ophthalmology 108 (1990): 1751–1757) have been used to ameliorate the damaging effects of constant light. There is no evidence, however, that these compounds will act to ameliorate other forms of photoreceptor degeneration and their administration can generate potentially harmful side effects. Further, these studies are limited because they utilize systemic delivery. Such delivery often provides an inadequate means of assessing the efficacy of a particular factor. It is difficult to assess the amount of agent that actually reaches the retina. A large amount of agent must be injected to attain a sufficient concentration at the site of the retina. In addition, systemic toxic effects may result from the injection of certain agents.

Other than the use of bFGF to delay inherited photoreceptor degeneration in RCS rats, there is no demonstrated use of any specific neurotrophic or other cellular factor to prevent injury or death of mammalian photoreceptors. In copending U.S. application Ser. No. 07/400,591 which is incorporated by reference herein, a BDNF expressing clone was isolated from a retina/cDNA library. Based on that discovery, as well as the expression for the first time of purified BDNF using recombinant technology, a means was provided for the use of a purified neurotrophic factor for the treatment of diseases such as retinitis pigmentosa and other retina/degenerations. As described in greater detail below, the efficacy of BDNF, in addition to other neurotrophic and cellular factors, has been demonstrated, providing the first pharmacological means to treat most forms of inherited, age-related or environmentally-induced retinal degenerations.

SUMMARY OF THE INVENTION

An object of the present invention is to provide a method of preventing injury or death of retinal neurons.

Another object of the invention is to provide a method of treating pathological diseases wherein degeneration of the retina occurs.

Yet another object of the invention is to provide a method of treating the living eye prior to or following exposure to light or other environmental trauma thereby preventing degeneration of retina/cells.

A further object of the present invention is to provide a method of preventing photoreceptor injury and degeneration in the living eye.

Another object of the invention is to provide a method of protecting retinal neurons without the induction of side effects.

Another object of the invention is to provide a method of allowing injured photoreceptors to recover or regenerate.

Another object of the invention is to provide an in vivo assay system for assessing the survival-promoting activity of neurotrophic and other cellular factors on retinal neurons and photoreceptors.

These and other objects are achieved by treating the eye with an effective amount of a neurotrophic factor such as brain-derived neurotrophic factor (BDNF), ciliary neurotrophic factor (CNTF), neurotrophin-3 (NT-3) or neurotrophin-4 (NT-4), or a cellular factor such as acidic fibroblast growth factor (aFGF), basic fibroblast growth factor (bFGF) plus heparin, aFGF plus heparin, interleukin-1 beta (IL-1β), tumor necrosis factor-alpha (TNF-α) and insulin-like growth factor-2 (IGF-2). Similar effects, but to a lesser degree, may be achieved using other neurotrophic or cellular factors that may, alone, or in combination with other factors described herein, have therapeutically beneficial effects. Such factors include nerve growth factor (NGF), heparin, epidermal growth factor (EGF), platelet derived growth factor (PDGF) and insulin-like growth factor-1 (IGF-1).

DETAILED DESCRIPTION OF THE INVENTION

Figure 1:
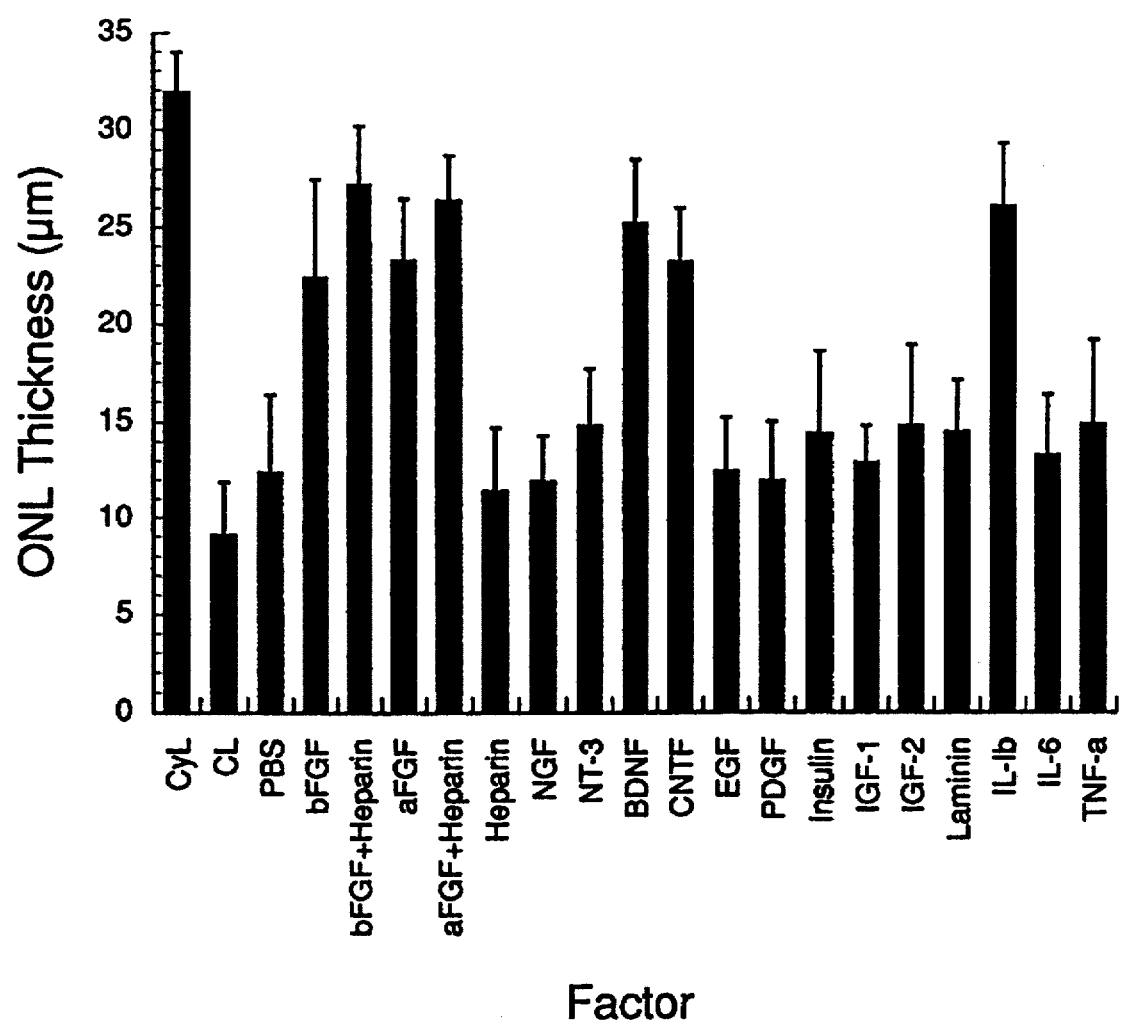
FIG. 1 is a histogram illustrating the degree of photoreceptor rescue obtained using the neurotrophic and cellular factors. CyL=cyclic light; CL=constant light; PBS= phosphate buffered saline; bFGF=basic fibroblast growth factor; aFGF=acidic fibroblast growth factor; NGF=nerve growth factor; NT-3=neurotrophin-3; BDNF=brain derived growth factor; CNTF=ciliary neurotrophic factor; EGF= epidermal growth factor; PDGF=platelet derived growth factor; IGF=insulin related growth factor; IL-6= interleukin-6 and TNF=tumor necrosis factor.

The present invention provides for the utilization of neurotrophic, as well as other cellular factors to delay, prevent or rescue photoreceptors, as well as other retinal cells, including neurons or supportive cells (e.g. Müller cells or RPE cells) from injury and degeneration. Other retinal neurons include, but are not limited to, retinal ganglion cells, displaced retinal ganglion cells, amacrine cells, displaced amacrine cells, horizontal and bipolar neurons.

As contemplated herein, neurotrophic or other cellular factors are utilized to treat any condition which results in injury or death of photoreceptors or other retinal cells. Examples of conditions include: retinal detachment; age-related and other maculopathies, photic retinopathies; surgery-induced retinopathies (either mechanically or light-induced); toxic retinopathies including those resulting from foreign bodies in the eye; diabetic retinopathies; retinopathy of prematurity; viral retinopathies such as CMV or HIV retinopathy related to AIDS; uveitis; ischemic retinopathies due to venous or arterial occlusion or other vascular disorders; retinopathies due to trauma or penetrating lesions of the eye; peripheral vitreoretinopathy; and inherited retinal degenerations.

The factors which are useful in practicing this invention include one or more neurotrophic factor such as brain-derived neurotrophic factor (BDNF), ciliary neurotrophic factor (CNTF), neurotrophin-3 (NT-3), neurotrophin-4 (NT- 4) or functional derivatives or analogs thereof, or one or more cellular factor such as basic fibroblast growth factor (bFGF) plus heparin, acidic fibroblast growth factor (aFGF), aFGF plus heparin, interleukin-1 beta (IL-1β), tumor necrosis factor-alpha (TNF-α), and insulin-like growth factor-2 (IGF-2), or functional derivatives or analogs thereof. Other factors that appears to be effective, but to a lesser extent, include nerve growth factor (NGF), heparin, epidermal growth factor (EGF), platelet derived growth factor (PDGF) and insulin-like growth factor-1 (IGF-1). A functional derivative of a factor is a compound which is an analog or an active fragment of the compound or its analog. Combinations of the neurotrophic factors and cellular factors may also be used to achieve optimum results.

Each of the factors utilized may be obtained by methods known by those skilled in the art. For example, they may be purified from a natural source. Alternatively, they may be made by recombinant means utilizing available sequence data. (See, for example, for CNTF; Masiakowski, et at. J. Neurochemistry 57 (1991): 1003–1012; NT-3; Maisonpierre, et al. Science 247 (1990): 1446–1451).

Of particular suitability in practicing the subject invention are the neurotrophic factors. As used herein, neurotrophic factors are proteins responsible for the development and maintenance of the nervous system. Widespread neuronal cell death accompanies normal development of the central and peripheral nervous systems, and apparently plays a crucial role in regulating the number of neurons which project to a given target field (Berg, D. K., 1982, Neuronal Development 297–331). Ablation and transplantation studies have shown that neuronal cell death results from the competition among neurons for limiting amounts of survival factors ("neurotrophic factors"). The important neurotrophic factors identified to date are NGF, BDNF, CNTF, NT-3 and NT-4.

In a preferred embodiment of the invention, BDNF is utilized to treat any condition which results in injury or death of photoreceptors or other retina-related cells. With the molecular cloning of BDNF, as well as the resultant production and purification of purified recombinant BDNF, as described in U.S. Ser. No. 400,591, it became possible to determine the physiological effects of BDNF on developing neurons, as well as to quantify the levels of BDNF in tissues by immunoassay and to localize BDNF in tissues using immunocytochemistry. Furthermore, a BDNF cDNA was found in a retinal library and BDNF mRNA was found to be expressed in adult retinas (Maisonpierre, et al. Neuron, 5 (1990): 501–509), suggesting production of the protein in the retina and a possible role for the factor in promoting retinal cell survival.

As described herein, treatment of the eye with BDNF results in the increased survival of photoreceptors upon exposure to environmental trauma such as light. Suprisingly, BDNF does not cause the influx of macrophages observed when treating the retina with bFGF. Furthermore, BDNF is not anticipated to have the side effects of bFGF as it does not have similar angiogenic or mitogenic properties.

In another preferred embodiment, ciliary neurotrophic factor (CNTF) is used to prevent or delay photoreceptor degeneration. CNTF, like BDNF, effectively protects photoreceptors without macrophage influx and the mitogenic and angiogenic properties of bFGF.

In still another embodiment, aFGF is used to prevent photoreceptor degeneration. This factor, unlike bFGF, appears to provide protection without the influx of macrophages observed when bFGF is used.

In yet another embodiment, bFGF is used in conjunction with a compound that suppresses the influx of macrophages observed using bFGF alone. Heparin appears to be useful for this purpose. Combinations of heparin and bFGF prevent photoreceptor injury without macrophage influx, and heparin enhances the action of aFGF, as well as bFGF (see FIG. 4).

In another embodiment, other factors such as IL-1β and TNF-α provide a substantial amount of retinal protection. IL-1β however, has been observed to cause folding and rosette formation and a somewhat greater incidence of macrophages than is observed in control retinas or those protected with BDNF or CNTF. Use of TNF-α may also be associated with a slightly greater than normal incidence of macrophages.

In additional embodiments, the light damage model may be used to evaluate the effect of various survival-promoting factors on the retina. As shown herein, the intravitreal administration of various factors into the eyes of albino rats enabled the rapid assessment of both the ability of the factors to rescue photoreceptors from degeneration and the side effects, such as incidence of macrophages, associated with each factor. Although the model described herein is the albino rat, the eyes of other albino mammals, such as mice and rabbits, are also useful for this purpose.

Although the light damage model has been used previously to assess the effect of various agents such as antioxidents on the retina, such studies have always been conducted using systemic (intraperitoneal) administration. As described herein, the intravitreal injection of potential survival promoting factors represents a novel method of assessing factors, with several advantages over systemic application. The amount of any specific agent that reaches the retina can be more accurately determined, since the eye is a round, relatively contained structure and the agent is injected directly into it. Morover, the amount of agent that need to be injected is miniscule compared to systemic injections. For example, a single microliter in volume (about 1 microgram of agent) is used for intravitreal injection, as compared to one to several milliliters (ten to several hundred milligrams of agent) necessary for systemic injections. In addition, the intravitreal route of administration avoids the potentially toxic effect of some agents.

According to the present invention, the factors used herein prevent the degeneration of retinal cells. It has been further observed that when animals that have been exposed to damaging light are returned to normal light, they will regenerate their inner and outer segments. Thus, the factors of the present invention are able not only to protect and prevent photoreceptors from degeneration, but also to promote regeneration of retinal cells.

The factors of the present invention can be delivered to the eye through a variety of routes. They may be delivered intraocularly, by topical application to the eye or by intraocular injection into, for example the vitreous or subretinal (interphotoreceptor) space. Alternatively, they may be delivered locally by insertion or injection into the tissue surrounding the eye. They may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membranes or fibers, biodegradable polymers, or proteinaceous material. The factors may be administered prior to the onset of the condition, to prevent its occurrence, for example, during surgery on the eye, or immediately after the onset of the pathological condition or during the occurrence of an acute or protracted condition.

The factors of the present invention may be modified to enhance their ability to penetrate the blood-retinal barrier. Such modifications may include increasing their lipophilicity by, for example, glycosylation, or increasing their net charge by methods known in the art.

The factors may be delivered alone or in combination, and may be delivered along with a pharmaceutically acceptable vehicle. Ideally, such a vehicle would enhance the stability and/or delivery properties. The invention also provides for pharmaceutical compositions containing the active factor or fragment or derivative thereof, which can be administered using a suitable vehicle such as liposomes, microparticles or microcapsules. In various embodiments of the invention, it may be useful to use such compositions to achieve sustained release of the active component.

The amount of factor which will be effective in the treatment of a particular disorder or condition will depend of the nature of the disorder or condition and can be determined by standard clinical techniques.

EXAMPLE 1

Use of Neurotrophic and Cellular Factors to Prevent Light Induced Photoreceptor Injury Albino rats of either the F344 or Sprague-Dawley strain were used at 2–5 months of age. The rats were maintained in a cyclic light environment (12 hr on: 12 hr off at an in-cage illuminance of less than 25 ft-c) for 9 or more days before being exposed to constant light. The rats were exposed to 1 or 2 weeks of constant light at an illuminance level of 115–200 ft-c (most rats received 125–170 ft-c) provided by two 40 watt General Electric "cool-white" fluorescent bulbs with a white reflector that was suspended 60 cm above the floor of the cage. During light exposure, rats were maintained in transparent polycarbonate cages with stainless steel wire-bar covers.

Two days before constant light exposure, rats anesthetized with a ketamine-xylazine mixture were injected intravitreally with 1 µl of the various factors dissolved in phosphate buffered saline (PBS) at a concentration of 50–1000 ng/µl. The injections were made with the insertion of a 32 gauge needle through the sclera, choroid and retina approximately midway between the ora serrata and equator of the eye. The factor-injected animals were compared to either uninjected littermates or to those that received intravitreal injections of 1 µl of PBS alone, as well as to animals that were not exposed to constant light. Controls included the injection of 1 µl of PBS alone, or the insertion of a dry needle with no injection. In all cases, the injections were made into the superior hemisphere of the eye.

Immediately following constant light exposure, the rats were killed by overdose of carbon dioxide followed immediately by vascular perfusion of mixed aldehydes. The eyes were embedded in epoxy resin for sectioning at 1 µm thickness to provide sections of the entire retina along the vertical meridian of the eye. The degree of light-induced retinal degeneration was quantified by two methods. The first was by measuring outer nuclear layer (ONL) thickness, which is used as an index of photoreceptor cell loss. A mean ONL thickness was obtained from a single section of each animal with the aid of a Bioquant morphometry system. In each of the superior and inferior hemispheres, ONL thickness was measured in 9 sets of 3 measurements each (total of 27 measurements in each hemisphere). Each set was centered on adjacent 440-µm lengths of retina (the diameter of the microscope field at 400× magnification). The first set of measurements was taken at approximately 440 µm from the optic nerve head, and subsequent sets were located more peripherally. Within each 440-µm length of retina, the 3 measurements were made at defined points separated from one another by 75 µm using an eyepiece micrometer. In this way, the 54 measurements in the two hemispheres sampled representative regions of almost the entire retinal section. The results obtained with each of the factors tested are summarized in FIG. 1.

The second method of assessing the degree of photoreceptor rescue was by a 0–4+ pathologist's scale of rescue, 4+ being maximal rescue and almost normal retinal integrity. The degree of photoreceptor rescue in each section, as based on comparison to the control eye in the same rat, was scored by four individuals. This method has the advantage of considering not only the ONL thickness, but also more subtle degenerative changes to the photoreceptor inner and outer segments, as well as spatial degenerative gradients within the eye. Data obtained from this method is summarized in FIG. 2. The number of eyes examined for each factor was 10 or more, except for insulin and laminin, which was 6 each.

RESULTS AND DISCUSSION

Figure 2:
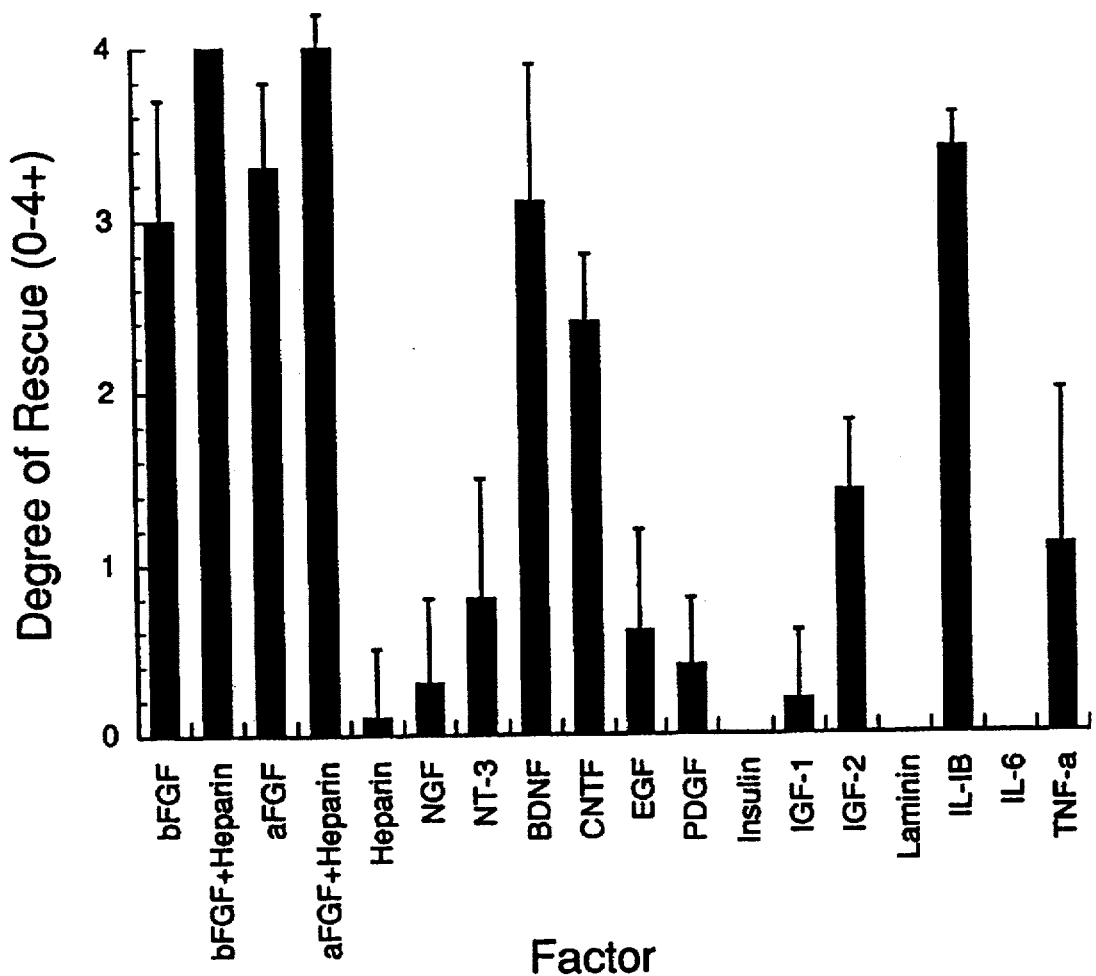
FIG. 2 is a histogram illustrating the ONL thickness obtained using the neurotrophic and cellular factors. (Abbreviations; same as FIG. 1).
Figure 3A:
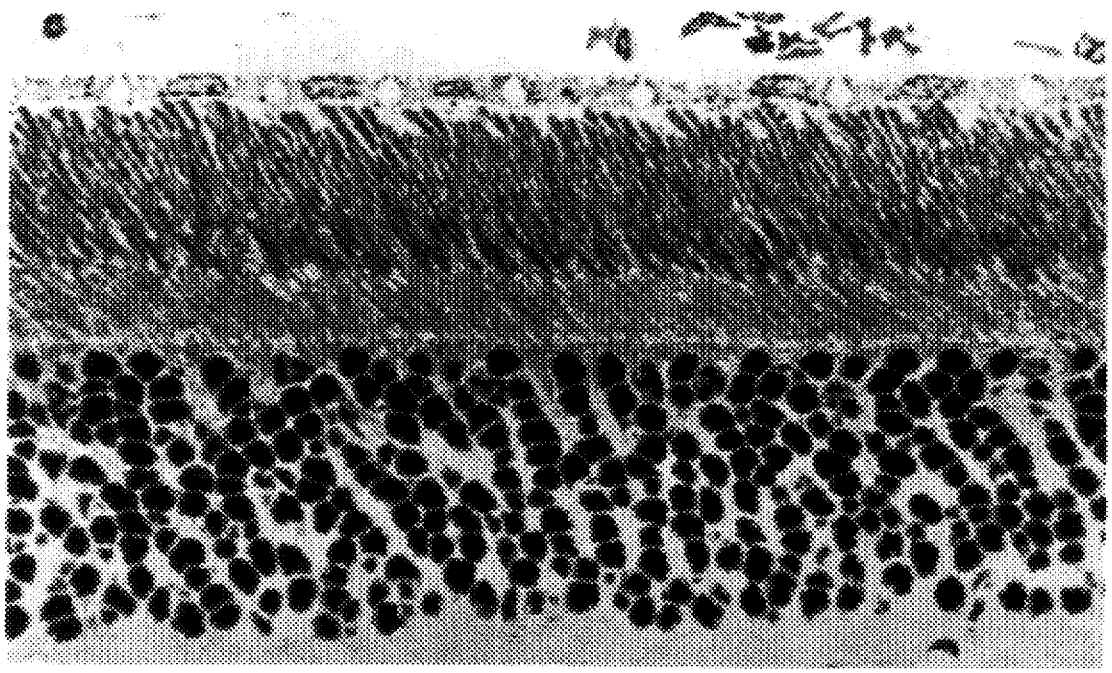
FIG. 3 is a composite of three light micrographs showing a) control retina from a rat not exposed to light; b) consol retina from a rat exposed to light after PBS injection; and c) BDNF-treated rat retina after exposure to light.
Figure 3B:
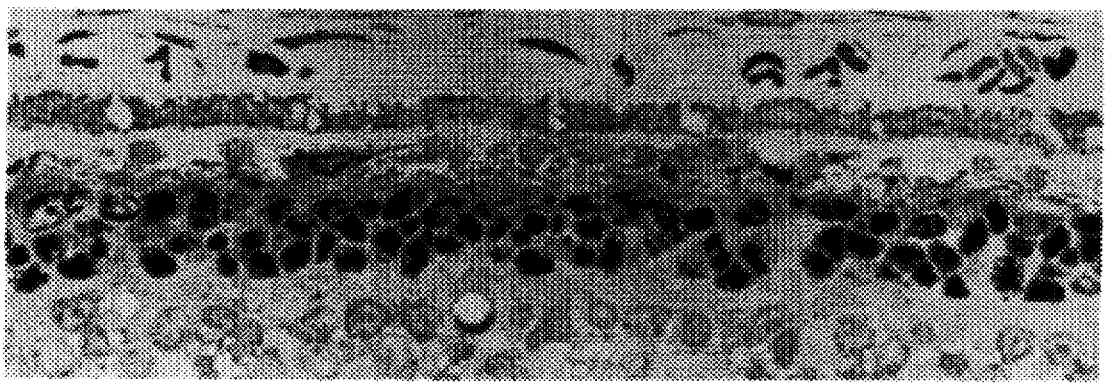
Figure 3C:
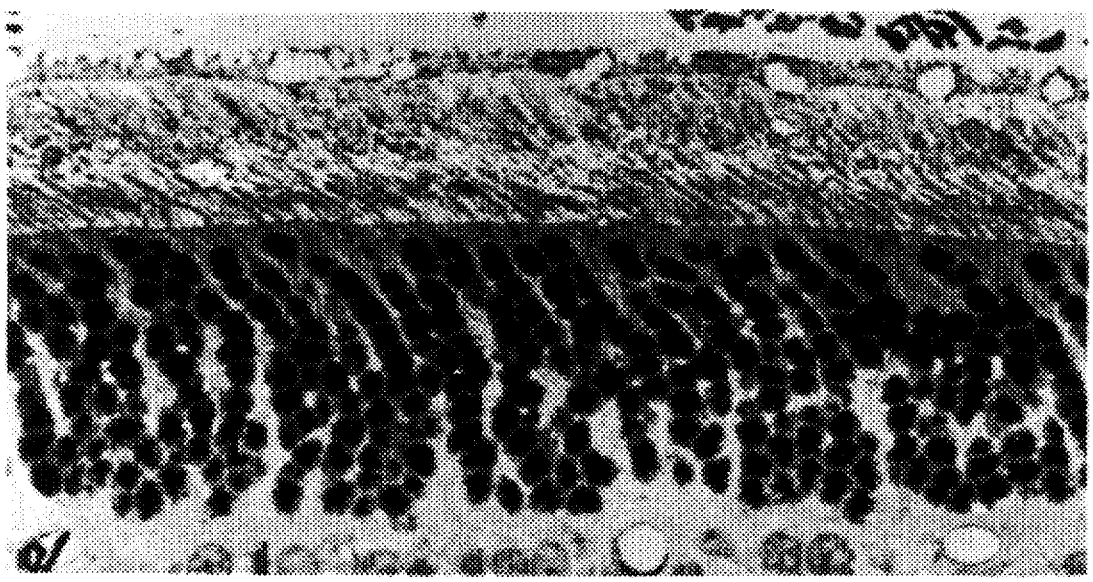
Figure 4:
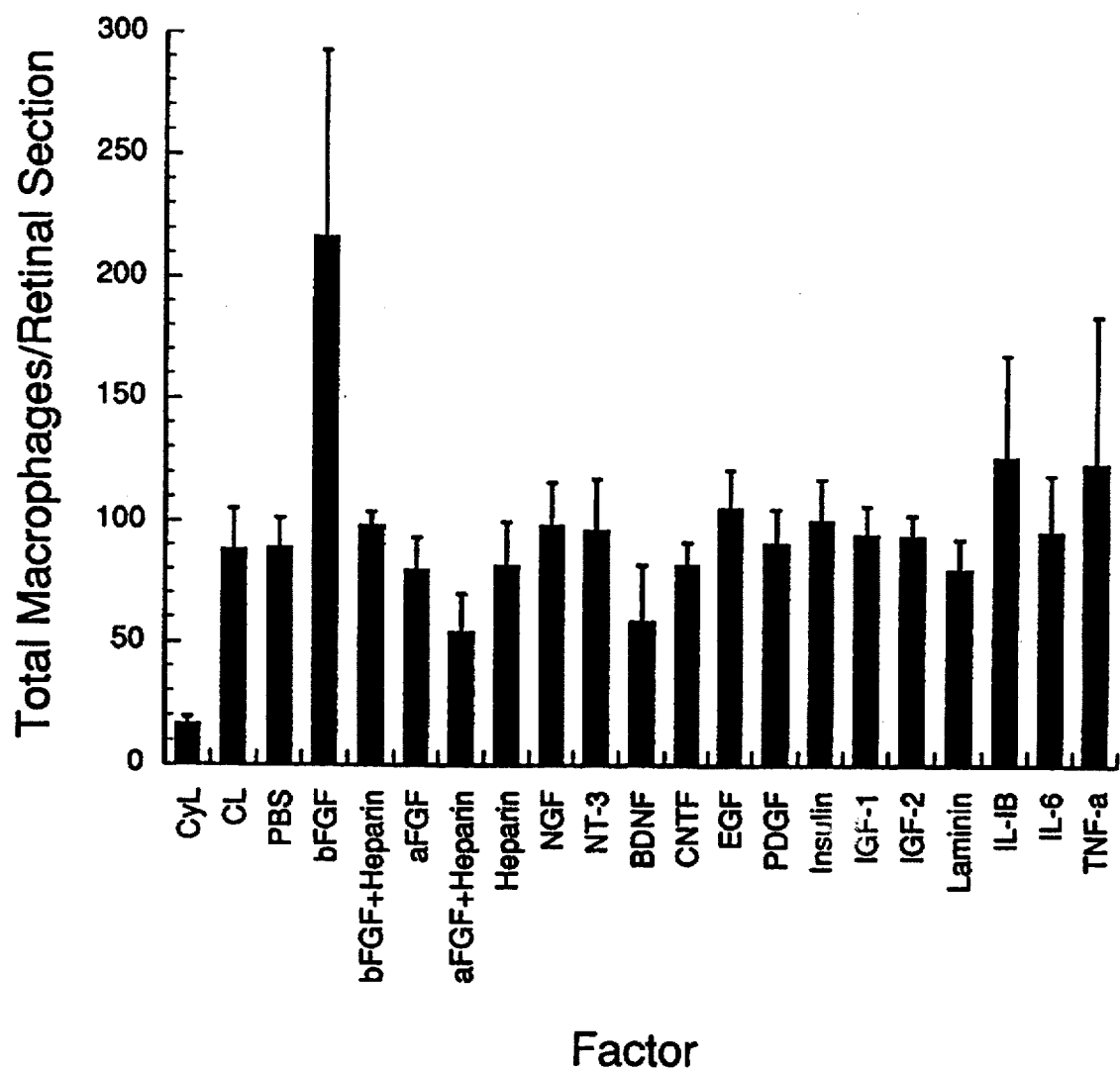
FIG. 4 is a histogram illustrating the degree of macrophage incidence observed using the neurotrophic and cellular factors. (Abbreviations; same as in FIG. 1).

The data obtained using the light damage model of photoreceptor injury is presented in FIGS. 1, 2 and 3. Neurotrophic factors BDNF and CNTF provided a high degree of rescue. The factors bFGF, aFGF, bFGF plus heparin, aFGF plus heparin, TNF-α, IL-1β, NT-3 and IGF-2 also provided a significant amount of rescue. Notably, all of the factors other than bFGF enhanced survival without inducing a high incidence of macrophages, as seen in FIG. 4 (IL-1β and TNF-α were associated with a slightly higher incidence of macrophages). Some factors actually suppressed the incidence of macrophages as compared to control retinas (retinas in the same animal that were injected with PBS). Such factors included BDNF, aFGF, and bFGF plus heparin.

Acidic fibroblast growth factor (aFGF), which had previously been reported to be ineffective as compared to bFGF in the RCS rat, was shown to provide significant protection of photoreceptors in the light-damage model. In addition, the influx of macrophages normally observed with injections of bFGF were not seen when bFGF was used in combination with heparin, thus eliminating a side effect that potentially would have obviated the use of bFGF.

Some degree of rescue, although to a lesser extent, was observed with heparin, PDGF, NGF, EGF and IGF-1.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. A method of reducing the degeneration of photoreceptors in a patient exposed to an environmental condition or having a pathological condition which causes such degeneration comprising administering into the eye of said patient an effective amount of CNTF.

2. The method of claim 1 wherein said administration is intraocular.

3. The method of claim 2 wherein said administration is into the vitreous or into the interphotoreceptor space.

4. The method of claim 1 wherein said environmental or pathological condition is retinal detachment, age-related or other maculopathies, photic retinopathies, surgery-induced retinopathies, toxic retinopathies, retinopathy of prematurity, retinopathies due to trauma or penetrating lesions of the eye, or inherited retinal degenerations.

5. A method of promoting the regeneration of outer segments of photoreceptors in a patient exposed to an environmental condition or having a pathological condition which causes photoreceptor degeneration comprising administering into the eye of said patient an effective amount of CNTF.

6. The method of claim 5 wherein said administration is intraocular.

7. The method of claim 6 wherein said administration is into the vitreous or into the interphotoreceptor space.

8. The method of claim 5 wherein said environmental or pathological condition is retinal detachment, age-related or other maculopathies, photic retinopathies, surgery-induced retinopathies, toxic retinopathies, retinopathy of prematurity, retinopathies due to trauma or penetrating lesions of the eye, or inherited retinal degenerations.

* * * * *